US009193873B2

(12) United States Patent
Wang et al.

(10) Patent No.: US 9,193,873 B2
(45) Date of Patent: *Nov. 24, 2015

(54) METHOD OF FACILITATING REMOVAL OF BIOORGANIC STAINS FROM SURFACES

(71) Applicants: Toyota Motor Engineering & Manufacturing North America, Inc., Erlanger, KY (US); Toyota Motor Corporation, Toyota (JP); Regents of the University of Minnesota, Minneapolis, MN (US)

(72) Inventors: Ping Wang, North Oaks, MN (US); Songtao Wu, Ann Arbor, MI (US); Hongfei Jia, Ann Arbor, MI (US); Masahiko Ishii, Okazaki (JP); Minjuan Zhang, Ann Arbor, MI (US); Xiaodong Tong, Circle Pines, MN (US)

(73) Assignees: Toyota Motor Engineering & Manufacturing North America, Inc., Erlanger, KY (US); Toyota Motor Corporation, Toyota (JP); Regents of the University of Minnesota, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/166,376

(22) Filed: Jan. 28, 2014

(65) Prior Publication Data
US 2014/0141490 A1 May 22, 2014

Related U.S. Application Data

(60) Division of application No. 12/891,424, filed on Sep. 27, 2010, now Pat. No. 8,679,825, which is a continuation-in-part of application No. 12/434,320, filed on May 1, 2009, now Pat. No. 8,252,571.

(51) Int. Cl.
| | |
|---|---|
| *C12N 9/28* | (2006.01) |
| *C09D 5/16* | (2006.01) |
| *C07K 17/08* | (2006.01) |
| *C08G 18/40* | (2006.01) |
| *C08G 18/42* | (2006.01) |
| *C08G 18/62* | (2006.01) |
| *C08G 18/64* | (2006.01) |
| *C08G 18/70* | (2006.01) |
| *C08G 18/79* | (2006.01) |
| *C09D 5/02* | (2006.01) |
| *C09D 175/04* | (2006.01) |
| *C12N 9/26* | (2006.01) |
| *C12N 11/08* | (2006.01) |
| *C09D 7/12* | (2006.01) |

(52) U.S. Cl.
CPC ............. *C09D 5/1637* (2013.01); *C07K 17/08* (2013.01); *C08G 18/4081* (2013.01); *C08G 18/42* (2013.01); *C08G 18/6216* (2013.01); *C08G 18/6446* (2013.01); *C08G 18/706* (2013.01); *C08G 18/792* (2013.01); *C09D 5/025* (2013.01); *C09D 7/1275* (2013.01); *C09D 7/1283* (2013.01); *C09D 175/04* (2013.01); *C12N 9/2411* (2013.01); *C12N 9/2414* (2013.01); *C12N 9/2417* (2013.01); *C12N 11/08* (2013.01)

(58) Field of Classification Search
None
See application file for complete search history.

(56) References Cited

U.S. PATENT DOCUMENTS

| | | | |
|---|---|---|---|
| 4,094,744 A | 6/1978 | Hartdegen et al. | |
| 4,098,645 A | 7/1978 | Hartdegen et al. | |
| 4,195,127 A | 3/1980 | Hartdegen et al. | |
| 4,195,129 A | 3/1980 | Fukui et al. | |
| 5,914,367 A | 6/1999 | Dordick et al. | |
| 6,015,783 A | 1/2000 | von der Osten et al. | |
| 6,291,582 B1 | 9/2001 | Dordick et al. | |
| 6,599,627 B2 | 7/2003 | Yeo et al. | |
| 6,855,746 B2 | 2/2005 | Yoshitake et al. | |
| 6,905,733 B2 * | 6/2005 | Russell et al. | 427/393.5 |
| 7,442,678 B2 | 10/2008 | Sandbach et al. | |
| 8,252,571 B2 | 8/2012 | Wang et al. | |
| 2011/0076738 A1 | 3/2011 | Wang et al. | |

FOREIGN PATENT DOCUMENTS

WO 2009155115 A2 12/2009

OTHER PUBLICATIONS

Studer et al., European Polymer Journal, 2005, vol. 41, p. 157-167.*
Keyes et al. "Crosslinkg Acrylic Solution Adhesives with Blocked Isocyanates", p. 83-90, www.pstc.org/files/public/Keyes.pdf, online 2006.*
Novick, S. et al., Protein-containing hydrophobic coatings and films, Biomaterials, 23: 441-448, 2002.
Drevon, G. et al., High-Activity Enzyme-Polyurethane Coatings, Biotechnology and Bioengineering, 79(7): 785-794, Sep. 30, 2002.

* cited by examiner

*Primary Examiner* — Kade Ariani
(74) *Attorney, Agent, or Firm* — Dinsmore & Shohl LLP

(57) ABSTRACT

Protein-polymer composite materials are provided according to embodiments of the present invention that include an admixture of a polymer resin, a surfactant and a non-aqueous organic solvent. An aqueous solution containing bioactive proteins is mixed with the admixture. The emulsion is mixed with a crosslinker to produce a curable composition. The curable composition is cured, thereby producing the protein-polymer composite material that is useful for facilitating removal of bioorganic stains.

5 Claims, 13 Drawing Sheets

A

B

METHOD OF FACILITATING REMOVAL OF BIOORGANIC STAINS FROM SURFACES

CROSS REFERENCE TO RELATED APPLICATIONS

This application is a divisional of and claims priority to U.S. patent application Ser. No. 12/891,424 filed Sep. 27, 2010, which is a continuation-in-part of and claims priority to U.S. patent application Ser. No. 12/434,320 filed May 1, 2009; the entire contents of these applications are incorporated herein by reference.

FIELD OF THE INVENTION

The present invention relates generally to coating compositions including bioactive substances such as a hydrolase. In specific embodiments, the invention relates to hydrolase-polymer composite materials for use in form of thin film coatings.

BACKGROUND OF THE INVENTION

Bioactive proteins are potentially useful in various applications. However, there is a continuing need for materials including bioactive substances for the removal of bioorganic stains, particularly food stains such as on clothing, cooking or eating surfaces, or anywhere food is prepared or consumed.

SUMMARY OF THE INVENTION

Methods according to embodiments of the present invention are provided which include formation of fine emulsion solution that contains bioactive proteins such as α-amylase dispersed in a continuous phase containing polymerizable ingredients, such that the proteins are entrapped and crosslinked with polymer upon the formation of the polymer network. The crosslinking of at least some of the protein to the polymer network along with the confinement of the protein in the polymer provides long-lasting activity of the protein ingredient in a coating formed using methods and materials described herein.

A method of facilitating removal of a bioorganic stain from a surface is provided including providing a curable polymeric coating including a polymer resin, a surfactant, a non-aqueous organic solvent, and a crosslinker, and associating an amylase or analogue thereof with the coating such that the amylase or analogue thereof is capable of enzymatically cleaving a component of a bioorganic stain following curing. The bioactive proteins included in the protein-polymer composite are selected according to the desired properties of the protein-polymer composite and examples of included bioactive proteins include, but are not limited to, one or more types of hydrolases, illustratively an amylase, illustratively an α-amylase.

The protein-polymer composite material optionally includes a polymer resin that is a hydroxyl-functionalized acrylate resin. A crosslinker is optionally a polyisocyanate.

One or more additives can be included in the admixture, the aqueous solution, the emulsion, and/or the curable composition.

The amylase is contained in the coatings in a particle with average particle size in the range of 1 nm to 10 μm (average diameter), inclusive.

Coatings optionally have a surface activity of at least 0.1 Unit/cm$^2$.

A bioorganic stain is optionally food, optionally mayonnaise illustratively light mayonnaise, barbeque sauce, tartar sauce, potato, fruit, or combinations thereof.

Coatings are optionally applied to a substrate prior to curing.

Curing of coatings is optionally achieved by thermal curing or actinic radiation.

A protein-polymer composite material according to embodiments of the present invention includes one or more amylases or analogues thereof dispersed in a two component solvent-borne polymer resin, wherein the average particle size of particles of amylases or analogues thereof in the protein-polymer composite material is in the range of 1 nm to 10 μm (average diameter), inclusive. The resins optionally include a hydroxyl-functionalized acrylate resin, a polyisocyanate crosslinker, or one or more additives. The amylase in particular embodiments of a protein-polymer composite material is optionally an α-amylase.

DETAILED DESCRIPTION OF THE INVENTION

Figure 1A:
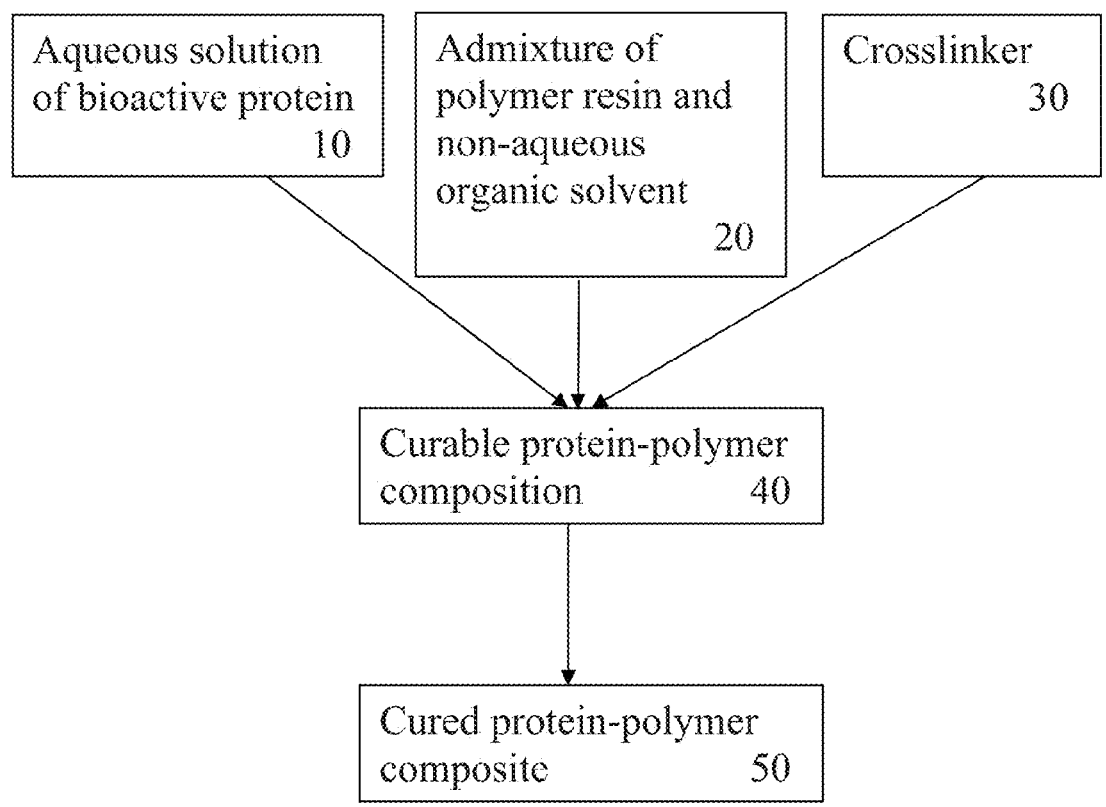
FIG. 1A is a flow diagram of a process to manufacture a bioactive material according to one embodiment of the present invention.

The following description of embodiment(s) of the invention is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

Protein-polymer composite materials are provided according to embodiments of the present invention for the facilitated removal of bioorganic stains. Protein-polymer composite materials according to the present invention are useful in numerous applications, including coatings, such as for biosensors, anti-fouling surfaces and biocatalytic devices.

It is appreciated that while the description herein is directed to coatings, the materials described herein may also be substrates or articles that do not require a coating thereon for promotion of active removal of a bioorganic stain. As such, the word "coating" as used herein means a material that is operable for layering on a surface of one or more substrates, or may comprise the substrate material itself. As such, the methods and compositions disclosed herein are generally referred to as a protein associated with a coating for exemplary purposes only. One of ordinary skill in the art appreciates that the description is equally applicable to substrates themselves.

A method of facilitating the removal of a bioorganic stain from a surface is provided including providing a curable polymeric coating comprising a polymer resin, a surfactant, a non-aqueous organic solvent, a crosslinker, and an amylase or analogue thereof to form a protein-polymer composite material wherein the amylase is capable of cleaving one or more components of a bioorganic stain prior to or following curing of the coating material.

A bioorganic stain as defined herein is a stain, mark, or residue left behind after an organic material contacts a surface. Illustrative examples of bioorganic stains include food, such as starch containing foods. Illustrative examples of starch containing foods include mayonnaises illustratively light mayonnaises, barbeque sauces, potatoes, fruits, or combinations thereof. Light mayonnaises are mayonnaises with a relatively increased level of starch typically sold as "light." Other sources of bioorganic stains are illustratively: insect wings, legs, or other appendages; bird droppings; fingerprints or residue left behind after a coating is contacted by an organism; or other sources of bioorganic stains recognized in the art. The protein-polymer coatings illustratively include one or more amylases or analogues thereof as an active agent for the facilitation of removal of a bioorganic stain. As such, any stain that contains one or more starches is operable for facilitated removal by a protein-polymer coating.

It was unexpectedly discovered that amylases are superior proteins for incorporation into protein-polymer materials. Amylases are both stable in polymeric materials and show unexpectedly high activity toward particular bioorganic stains such as stains from foods. More surprisingly, amylases show significant heat and time stability when incorporated into 2K solvent borne (SB) coatings as compared to other coating types such as water borne (WB) coatings. This unexpectedly high stability is particularly observed in 2K solvent-borne polyurethane coatings.

Amylases are forms of hydrolases that are physiologically responsible for breaking down starches. At least three categories of amylases are known in the art. α-amylases (EC 3.2.1.1) are calcium dependent metalloproteases that cleave starches at multiple locations. β-amylases (EC 3.2.1.2) are more specific for cleavage sites on a starch chain preferring cleavage at the non-reducing end by hydrolysis of the second α-1,4 glycosidic bond to release maltose. G-amylases (EC 3.2.1.3) are most active in acidic environments and are capable of cleaving α(1-6) glycosidic linkages of starches as well as α(1-4) glycosidic linkages at the nonreducing end of amylose and amylopectin. Amylases are found in and obtained from numerous organisms illustratively including fungi, bacteria, plants, and animals.

Amylases or analogues thereof are optionally thermostable amylases such as those synthesized by *Bacillus stearothermophilus*, cold-activated amylases such as that secreted by the Antarctic bacterium *Alteromonas haloplanctis*, other amylases such as those produced by bacteria such as *Bacillus subtilis*, or amylases produced by gram-negative bacteria such as *E. coli*. Specific examples of bacterial sources of amylases illustratively include *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus thuringiensis*, or *Streptomyces lividans* or *Streptomyces murinus*. Illustrative examples of yeast strains illustratively include strains of *Saccharomyces* such as *Saccharomyces cerevisiae* or strains of *Schizosaccharomyces*. Illustratively, an amylase is obtained from a fillimentous fungus such as species of *Aspergillus*, e.g., *Aspergillus oryzae* or *Aspergillus niger*.

One specific example of an amylase is the α-amylase from *Bacillus subtilis* available from Sigma-Aldrich (St. Louis, Mo.) or from Amano Enzyme, Inc. (Nagoya, Japan). An α-amylase optionally has an activity of greater than 200 U/mg where a unit (U) is defined as the amount of enzyme in solution or in a coating area capable of liberating 1 μmole of maltose per minute at pH 6.9 and 25° C. from the substrate potato starch.

A "protein" as defined herein is a "peptide," "polypeptide," and "bioactive protein" (terms used herein synonymously) and is intended to mean a natural or synthetic compound containing two or more amino acids having some level of activity toward a natural or synthetic substrate of a wild-type amylase. A wild-type amylase is a protease that has an amino acid sequence identical to that found in an organism in nature. An illustrative example of a wild-type amylase is that found at GenBank Accession No. ADH93706 and SEQ ID NO: 1. An example of a DNA sequence encoding a wild-type amylase is found at GenBank Accession No. GU979529 and SEQ ID NO: 2.

A protein functions with one or more cofactor ions or proteins. A cofactor ion is illustratively a zinc, cobalt, or calcium.

Methods of screening for protein enzymatic activity are known and standard in the art. Illustratively, screening for enzymatic activity in an amylase or analogue thereof includes contacting an amylase or analogue thereof with a natural or synthetic substrate of a protease and measuring the enzymatic cleavage of the substrate. Illustrative substrates for this purpose include potato starch which is cleaved illustratively by α-amylase to yield free maltose. Other suitable substrates, both physiological and synthetic are known in the art.

It is recognized that numerous analogues of protein are operable and within the scope of the present invention including amino acid substitutions, alterations, modifications, or other amino acid changes that increase, decrease, or not alter the function of the protease protein sequence. Several post-translational modifications are similarly envisioned as within the scope of the present invention illustratively including incorporation of a non-naturally occurring amino acid, phosphorylation, glycosylation, and addition of pendent groups such as biotinylation, fluorophores, lumiphores, radioactive groups, antigens, or other molecules.

In some embodiments an analogue of an amylase is present in a coating. An analog is optionally a protein with one or more amino acid substitutions, alterations, modifications, or other amino acid changes that increase, decrease, or not alter the function of the protein relative to a wild-type protein. Several post-translational modifications are similarly envisioned as within the scope of the present invention illustratively including incorporation of a non-naturally occurring amino acid, phosphorylation, glycosylation, addition of pendent groups such as biotinylation, fluorophores, lumiphores, radioactive groups, antigens, or other molecules. An analogue of an amylase is optionally a fragment of an amylase. An analogue of an amylase is a polypeptide that has some level of activity toward a natural or synthetic substrate of an amylase. An analogue optionally has between 0.1% and 200% the activity of a wild-type protease. An analogue of an amylase is optionally a wild-type amylase that is altered in at least one property relative to the wild-type enzyme. Such properties illustratively include substrate specificity, substrate binding, substrate cleavage pattern, thermal stability, pH/activity profile, pH/stability profile, stability towards oxidation, $Ca^{2+}$ dependency, specific activity, solubility, or combinations thereof. Methods of synthesizing an amylase, modifying an amylase, testing for activity or a property of an amylase analogue, or expressing an amylase of analogue thereof are illustratively described in U.S. Pat. No. 7,432,099, the contents of which are incorporated herein by reference.

Amino acids present in an amylase or analog thereof include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine; as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxylsoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. An amylase includes proteins having between 2 and about 1000 amino acids or having a molecular weight in the range of about 150-350,000 Daltons.

A protein is obtained by any of various methods known in the art illustratively including isolation from a cell or organism, chemical synthesis, expression of a nucleic acid sequence, and partial hydrolysis of proteins. Chemical methods of protein synthesis are known in the art and include solid phase peptide synthesis and solution phase peptide synthesis or by the method of Hackeng, T M, et al., *Proc Natl Acad Sci USA*, 1997; 94(15):7845-50, the contents of which are incorporated herein by reference. A protein may be a naturally occurring or non-naturally occurring protein. The term "naturally occurring" refers to a protein endogenous to a cell, tissue or organism and includes allelic variations. A non-naturally occurring protein is synthetic or produced apart from its naturally associated organism or modified and is not found in an unmodified cell, tissue or organism.

Modifications and changes can be made in the structure of a protein and still obtain a molecule having similar characteristics as protein (e.g., a conservative amino acid substitution). For example, certain amino acids can be substituted for other amino acids in a sequence without appreciable loss of activity or optionally to reduce or increase the activity of an unmodified protein. Because it is the interactive capacity and nature of a protein that defines that protein's biological functional activity, certain amino acid sequence substitutions can be made in a protein sequence and nevertheless obtain a protein with like or other desired properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution using amino acids whose hydropathic indices are within ±2, those within ±1, and those within ±0.5 are optionally used.

Substitution of like amino acids can also be made on the basis of hydrophilicity. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain an enzymatically equivalent polypeptide. In such changes, the substitution of amino acids whose hydrophilicity values are within ±2, those within ±1, and those within ±0.5 are optionally used.

Amino acid substitutions are optionally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Be, Leu). Embodiments of this disclosure thus contemplate functional or biological equivalents of a protein as set forth above. In particular, embodiments the proteins can include analogues having about 50%, 60%, 70%, 80%, 90%, 95%, or 99% sequence identity to a wild-type protein.

It is further appreciated that the above characteristics are optionally taken into account when producing a protein with reduced or improved enzymatic activity. Illustratively, substitutions in a substrate binding site, exosite, cofactor binding site, catalytic site, or other site in a protein may alter the activity of the protein toward a substrate. In considering such substitutions the sequences of other known naturally occurring or non-naturally occurring proteins may be taken into account. Illustrative examples of substitutions to a protein operable include those described in U.S. Pat. No. 7,432,099, the contents of which are incorporated herein by reference. Similar substitutions at homologous regions in other amylases are similarly operable, and practice of substitutions at such locations and others as well as operable substitutions are within the skill in the art, are regularly practiced, and are performed without undue experimentation. Similarly, it is within the level of skill in the art and routine practice to undertake site directed mutagenesis and screen for subsequent protein activity such as by the methods of De Kreig, *Eur J Biochem,* 2001; 268(18):4985-4991 for which this reference is similarly incorporated herein by reference.

A protein is illustratively recombinant. Methods of cloning, synthesizing or otherwise obtaining nucleic acid sequences encoding a protease are known and standard in the art that are equally applicable to a protein such as an amylase. Similarly, methods of cell transfection and protein expression are similarly known in the art and are applicable herein. Exemplary cDNA encoding the protein sequence of SEQ ID NO: 1 is the nucleotide sequence found at accession number and SEQ ID NO: 2.

A protein may be coexpressed with associated tags, modifications, other proteins such as in a fusion peptide, or other modifications or combinations recognized in the art. Illustrative tags include 6XHis, FLAG, biotin, ubiquitin, SUMO, or other tag known in the art. A tag is illustratively cleavable such as by linking to lipase or an associated protein via an enzyme cleavage sequence that is cleavable by an enzyme known in the art illustratively including Factor Xa, thrombin, SUMOstar protein as obtainable from Lifesensors, Inc., Malvern, Pa., or trypsin. It is further appreciated that chemical cleavage is similarly operable with an appropriate cleavable linker.

Protein expression is illustratively accomplished from transcription of a protein nucleic acid sequence, illustratively that of SEQ ID NO: 2, translation of RNA transcribed from the protease nucleic acid sequence or analogues thereof. An analog of a nucleic acid sequence is any sequence that when translated to protein will produce a protein analogue. Protein expression is optionally performed in a cell based system such as in *E. coli*, Hela cells, or Chinese hamster ovary cells. It is appreciated that cell-free expression systems are similarly operable.

A method of facilitating bioorganic stain removal uses a composition that includes one or more proteins incorporated into a coating. The protein is optionally non-covalently associated and/or covalently attached to the coating material or is otherwise associated therewith such as by bonding to the surface or by intermixing with the coating material during manufacture such as to produce entrapped protease. In some embodiments the protease is covalently attached to the coating material either by direct covalent interaction between the protease and one or more components of the coating material or by association via a link moiety such as that described in U.S. Pat. App. Publ. No. 2008/0119381, the contents of which are incorporated herein by reference.

There are several ways to associate a protein with a coating. One of method of association involves the application of covalent bonds. Specifically, free amine groups of the protein may be covalently bound to an active group of the substrate. Such active groups include alcohol, thiol, aldehyde, carboxylic acid, anhydride, epoxy, ester, or any combination thereof. This method of incorporating protein delivers unique advantages. First, the covalent bonds tether the proteins permanently to the substrate and thus place them as an integral part of the final composition with much less, if any at all, leakage of the protein. Second, the covalent bonds provide extended enzyme lifetime. Over time, proteins typically lose activity because of the unfolding of their polypeptide chains. Chemical binding such as covalent bonding effectively restricts such unfolding, and thus improves the protein life. The life of a protein is typically determined by comparing the amount of activity reduction of a protein that is free or being physically adsorbed with that of a protein covalently-immobilized over a period of time.

Proteins are optionally uniformly dispersed throughout the coating network to create a substantially homogenous protein platform. In so doing, proteins may be first modified with polymerizable groups. The modified proteins may be solubilized into organic solvents in the presence of surfactant, and thus engage the subsequent polymerization with monomers such as methyl methacrylate (MMA) or styrene in the organic solution. The resulting composition optionally includes protein molecules homogeneously dispersed throughout the network.

Proteins are optionally attached to surfaces of a substrate. An attachment of proteins corresponding to approximately 100% surface coverage was achieved with polystyrene particles with diameters range from 100 to 1000 nm.

Chemical methods of protein attachment to materials will naturally vary depending on the functional groups present in the protein and in the material components. Many such methods exist. For example, methods of attaching proteins (such as enzymes) to other substances are described in O'Sullivan et al, *Methods in Enzymology,* 1981; 73:147-166 and Erlanger, *Methods in Enzymology,* 1980; 70:85-104, each of which are herein incorporated herein by reference.

Proteins are optionally present in a coating that is layered upon a substrate wherein the protein is optionally entrapped in the coating material, admixed therewith, modified and integrated into the coating material or layered upon a coating similar to the mechanisms described for interactions between a protein and substrate material.

Methods of preparing protein-polymer composite materials illustratively include use of aqueous solutions of protease and non-aqueous organic solvent-borne polymers to produce bioactive organic solvent-borne protein-polymer composite materials.

Methods of preparing protein-polymer composite materials are illustratively characterized by dispersion of protein in solvent-borne resin prior to curing and in the composite materials, in contrast to forming large aggregates of the bioactive proteins which diminish the functionality of the protein and protein-polymer composite materials. Proteins are optionally dispersed in the protein-polymer composite material such that the proteins are unassociated with other bioactive proteins and/or form relatively small particles of associated proteins. Illustratively, the average particle size of amylase particles in the protein-polymer composite material is less than 10 µm (average diameter) such as in the range of 1 nm to 10 µm, inclusive.

Curable protein-polymer compositions are optionally two-component solvent-borne (2K SB) compositions. Optionally, one component systems (1K) are similarly operable. Illustratively, a protein is entrapped in a coating material such as a latex or enamel paint, varnish, polyurethane gels, or other coating materials. Illustrative examples of incorporating enzymes into paints are presented in U.S. Pat. No. 5,998,200, the contents of which are incorporated herein by reference.

Processes for preparation of protein-polymer composite materials are provided according to embodiments of the present invention which include use of aqueous solutions of bioactive proteins and non-aqueous organic solvent-borne polymers to produce bioactive organic solvent-borne protein-polymer composite materials. These inventive processes are also referred to as "direct dispersion" processes herein.

Figure 1B:
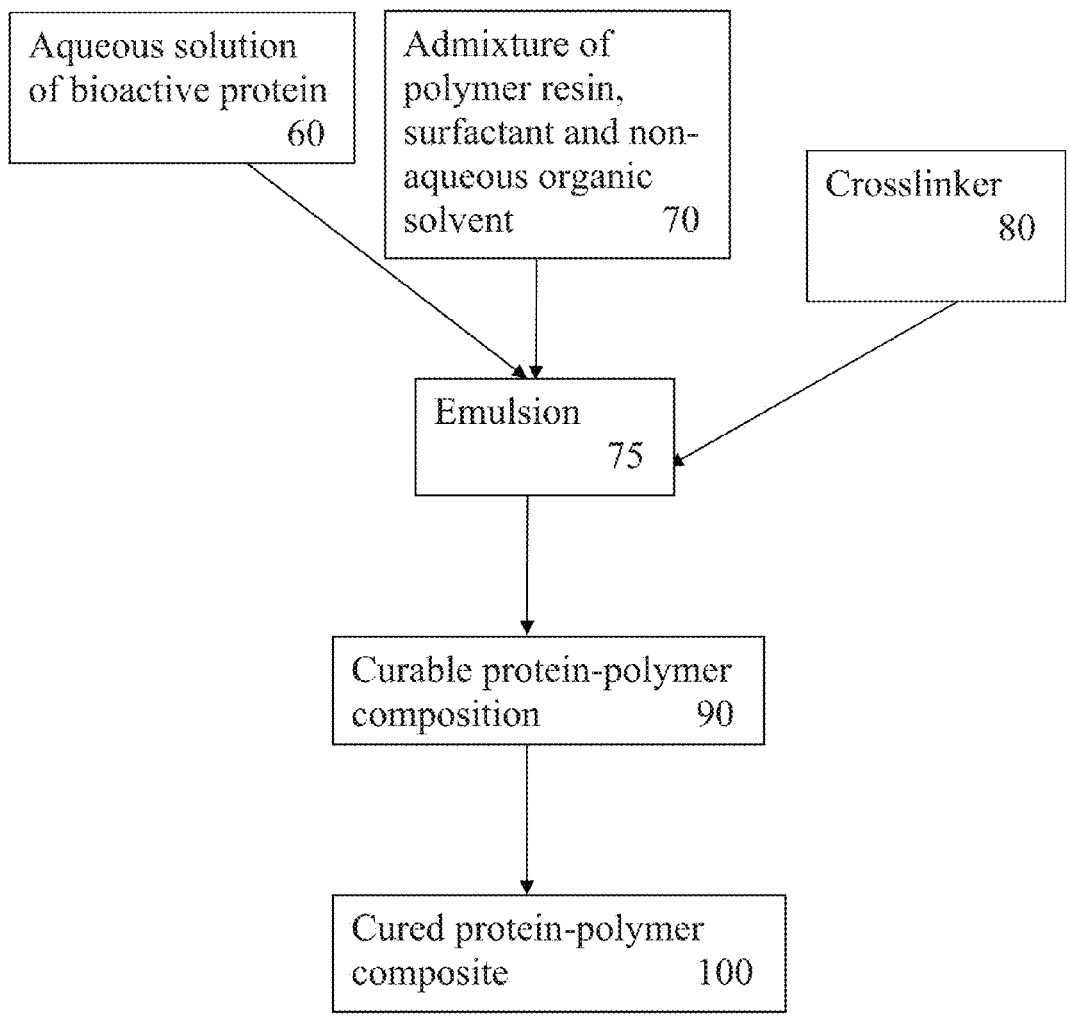
FIG. 1B is a flow diagram of a process to manufacture a bioactive material according to one embodiment of the present invention.

Processes provided according to embodiments of the present invention are generally illustrated in the flow diagrams shown in FIGS. 1A and 1B. As indicated in FIG. 1A, an aqueous solution of a bioactive protein, 10, and an admixture, 20, of a polymer resin and an organic solvent, are mixed to produce a curable protein-polymer composition, 40. Optionally, a crosslinker, 30, is present in the curable protein-polymer composition, 40, depending on the polymer resin used and the curing modality selected. Curing of the composition is performed to produce a cured protein-polymer composite material, 50.

As shown in FIG. 1B, an aqueous solution of a bioactive protein, 60, and an admixture, 70, of a polymer resin, surfactant and a non-aqueous organic solvent, are optionally mixed to produce an emulsion, 75. A crosslinker, 80, is added to the emulsion, 75, depending on the polymer resin used and the curing modality selected, producing a curable protein-polymer composition, 90. The curable protein-polymer composition 90 is optionally cured to produce a protein-polymer composite material, 100.

Processes for preparation of protein-polymer composite materials according to embodiments of the present invention are characterized by dispersion of proteins in solvent-borne resin prior to curing and in the composite materials, in contrast to forming large aggregates of the bioactive proteins which diminish the functionality of the bioactive proteins and protein-polymer composite materials. In some embodiments, bioactive proteins are dispersed in the protein-polymer composite material such that the bioactive proteins are unassociated with other bioactive proteins and/or form relatively small particles of associated proteins. Thus, in embodiments, the average particle size of bioactive protein particles in the protein-polymer composite material is less than 10 µm (average diameter) such as in the range of 1 nm to 10 µm, inclusive.

Curable protein-polymer compositions according to embodiments of the present invention include two-component solvent-borne (2K SB) compositions optionally where the two components are mixed shortly before use, for instance, application of the curable protein-polymer composition to a substrate to form a bioactive coating such as a bioactive clear coat. Generally described, the first component contains a crosslinkable polymer resin and the second component contains a crosslinker. Thus, for example, referring to FIG. 1B, the emulsion 75 is a first component containing a crosslinkable resin and the crosslinker 80 is a second component, mixed together to produce the curable protein-polymer composition.

A polymer resin can be any film-forming polymer useful in coating compositions, such as clear coat compositions. Such polymers illustratively include, aminoplasts, melamine formaldehydes, carbamates, polyurethanes, polyacrylates, epoxies, polycarbonates, alkyds, vinyls, polyamides, polyolefins, phenolic resins, polyesters, polysiloxanes; and combinations of any of these or other polymers.

In particular embodiments, a polymer resin included in a curable composition is crosslinkable. For example, a crosslinkable polymer has a functional group characteristic of a crosslinkable polymer. Examples of such functional groups illustratively include acetoacetate, acid, amine, carboxyl, epoxy, hydroxyl, isocyanate, silane, and vinyl.

A crosslinking agent is optionally included in the curable composition. The particular crosslinker selected depends on the particular polymer resin used. Non-limiting examples of crosslinkers include compounds having functional groups such as isocyanate functional groups, epoxy functional groups, aldehyde functional groups, and acid functionality.

In particular embodiments, a polymer resin is a hydroxyl-functional acrylic polymer and the crosslinker is a polyisocyanate.

A polyisocyanate, optionally a diisocyanate is a crosslinker reacted with the hydroxyl-functional acrylic polymer according to embodiments of the present invention. Aliphatic polyisocyanates are optionally used in protein-polymer composite materials for clearcoat applications such as in automotive clearcoat applications. Non-limiting examples of aliphatic polyisocyanates include 1,4-butylene diisocyanate, 1,4-cyclohexane diisocyanate, 1,2-diisocyanatopropane, 1,3-diisocyanatopropane, ethylene diisocyanate, lysine diisocyanate, 1,4-methylene bis(cyclohexyl isocyanate), diphenylmethane 4,4'-diisocyanate, an isocyanurate of diphenylmethane 4,4'-diisocyanate, methylenebis-4,4'-isocyanatocyclohexane, 1,6-hexamethylene diisocyanate, an isocyanurate of 1,6-hexamethylene diisocyanate, isophorone diisocyanate, an isocyanurate of isophorone diisocyanate, p-phenylene diisocyanate, toluene diisocyanate, an isocyanurate of toluene diisocyanate, triphenylmethane 4,4',4"-triisocyanate, tetramethyl xylene diisocyanate, and meta-xylene diisocyanate.

Proteins selected for inclusion in a particular protein-polymer composite material depend on the intended application of the material and one of skill in the art will be able to select one or more appropriate proteins.

Proteins can be obtained from commercial sources, isolated from natural sources such as an organism or cell that produces the protein or can be synthesized using well-known chemical and/or recombinant methodology.

Bioactive proteins are included in composite materials according to embodiments of the present invention in amounts ranging from 0.1-50% weight percent of the total weight of the composite material composition.

Curing modalities are those typically used for conventional curable polymer compositions.

Protein-polymer composite materials are optionally thermoset protein-polymer composite materials. For example, thermal curing is used in particular embodiments. A thermal polymerization initiator is optionally included in a curable composition according to embodiments of the present invention. Thermal polymerization initiators include free radical initiators such as organic peroxides and azo compounds. Examples of organic peroxide thermal initiators include benzoyl peroxide, dicumylperoxide, and lauryl peroxide. An exemplary azo compound thermal initiator is 2,2'-azobisisobutyronitrile.

Conventional curing temperatures and curing times can be used according to embodiments of the present invention. For example, the curing time at specific temperatures, or under particular curing conditions, is determined by the criteria that the cross-linker functional groups are reduced to less than 5% of the total present before curing. Cross-linker functional groups can be quantitatively characterized by FT-IR or other suitable method. For example, the curing time at specific temperatures, or under particular curing conditions, for a polyurethane protein-polymer composite of the present invention can be determined by the criteria that the cross-linker functional group NCO is reduced to less than 5% of the total present before curing. The NCO group can be quantitatively characterized by FT-IR. Additional methods for assessing the extent of curing for particular resins are well-known in the art.

Curing may include evaporation of a solvent in particular embodiments.

Optionally, a curable composition is cured by exposure to actinic radiation, such as ultraviolet, electron beam, microwave, visible, infrared, or gamma radiation.

Some embodiments include addition of one or more additives for modifying the properties of the protein-polymer composite material and/or the admixture of organic solvent and polymer resin, the aqueous bioactive protein solution, the emulsion, and/or the curable composition. Illustrative examples of such additives include a UV absorbing agent, a plasticizer, a wetting agent, a preservative, a surfactant, a lubricant, a pigment, a filler and an additive to increase sag resistance. Such additives, their amounts, sources, and uses are well known in the art.

Some embodiments include an admixture of a polymer resin, a surfactant and a non-aqueous organic solvent, mixed to produce an emulsion. The term "surfactant" refers to a surface active agent that reduces the surface tension of a liquid in which it is dissolved, or that reduces interfacial tension between two liquids or between a liquid and a solid.

Surfactants used can be any of a variety of surfactants including amphoteric, silicone-based, fluorosurfactants, anionic, cationic and nonionic such as described in K. R. Lange, Surfactants: A Practical Handbook, Hanser Gardner Publications, 1999; and R. M. Hill, Silicone Surfactants, CRC Press, 1999, the contents of each of which are incorporated herein by reference. Illustrative examples of anionic surfactants include alkyl sulfonates, alkylaryl sulfonates, alkyl sulfates, alkyl and alkylaryl disulfonates, sulfonated fatty acids, sulfates of hydroxyalkanols, sulfosuccinic acid esters, sulfates and sulfonates of polyethoxylated alkanols and alkylphenols. Illustrative examples of cationic surfactants include quaternary surfactants and amineoxides. Examples of nonionic surfactants include alkoxylates, alkanolamides, fatty acid esters of sorbitol or manitol, and alkyl glucamides. Illustrative examples of silicone-based surfactants include siloxane polyoxyalkylene copolymers.

In some embodiments no surfactant is intentionally added to the aqueous bioactive protein solution and the aqueous bioactive protein solution is substantially free of surfactant. The term "substantially free" refers to the total absence or near-total absence of surfactant in the aqueous bioactive protein solution.

Components used in processes according to embodiments of the present invention are used in amounts described herein, although more or less can be used.

A polymer resin, or mixture of polymer resins, is present in amounts in the range of about 10-90 weight % of the admixture of the polymer resin or polymer resins, solvent and surfactant. In embodiments of the present invention, a polymer resin, or mixture of polymer resins, is present in amounts in the range of about 20-60 weight % of the admixture. A solvent used as a diluent of the polymer resin or resins is typically present in amounts in the range of about 1-50 weight % of the admixture. In embodiments of the present invention, a solvent used as a diluent of the polymer resin or resins is present in amounts in the range of about 2-30 weight % of the admixture. A surfactant is typically present in amounts in the range of about 0.1-5 weight % of the admixture. In embodiments of the present invention, a solvent used as a diluent of the polymer resin or resins is present in amounts in the range of about 0.2-4 weight % of the admixture.

A polymer resin, or mixture of polymer resins, is present in amounts in the range of about 10-90 weight % of the curable composition. In embodiments of the present invention, a polymer resin, or mixture of polymer resins, is present in amounts in the range of about 20-60 weight % of the curable composition. A solvent used as a diluent of the polymer resin or resins is typically present in amounts in the range of about 1-50 weight % of the curable composition. In embodiments of the present invention, a solvent used as a diluent of the polymer resin or resins is present in amounts in the range of about 2-30 weight % of the curable composition. One or more crosslinkers is present in the curable composition depending on the resin used and the curing modality, in amounts in the range of about 1-30 weight % of the curable composition.

A surfactant added to the admixture of polymer resin or resins and solvent.

In particular embodiments, a non-aqueous organic solvent having a log P in the range of −0.5-2, inclusive, is used. In embodiments of the present invention, a non-aqueous organic solvent having a log P in the range of −0.5-2, inclusive is used as a diluent for a polymer resin, for example, to adjust the viscosity of the polymer resin.

The term "log P" refers to the partition coefficient of a substance. The log P of a substance is the base ten logarithm of the ratio of solubility of the substance in n-octanol to solubility of the substance in water. Log P values for many organic solvents are known, for example as described in Leo A, Hansch C, and Elkins D (1971). "Partition coefficients and their uses". *Chem Rev* 71 (6): 525-616. Log P values can also be calculated as described, for example, in Sangster, James (1997). *Octanol-Water Partition Coefficients: Fundamentals and Physical Chemistry, Vol. 2 of Wiley Series in Solution Chemistry*. Chichester: John Wiley & Sons Ltd.

Table 1 shows correlation of log P values with retention of incorporated bioactive protein activity and polyacrylate polyol resin compatibility.

TABLE 1

Solvent compatibility with polyacrylate polyol polymer resins, enzyme activity and stability

| Solvent | Log P | Compatible with resins | Initial specific activity (Unit/cm$^2$) | Half life of coating incubated at 103° C. (hours)* |
|---|---|---|---|---|
| Acetone | −0.23 | Yes | 1.75 | 30 |
| Methyl ethyl ketone | 0.29 | Yes | 1.48 | 59 |
| Ethyl acetate | 0.7 | Yes | 1.32 | 75 |
| Methyl isobutyl ketone | 1.31 | Yes | 1.40 | 93 |
| Butyl acetate | 1.7 | Yes | 1.70 | 154 |
| Toluene | 2.5 | Yes | 1.56 | 14 |
| Hexane | 3.5 | No | N/A | N/A |
| Isooctane | 4.5 | No | N/A | N/A |

*Coatings were cured by exposure to 80° C. for 30 minutes and then room temperature for one week before incubation in an oven at 103° C. to evaluate stability of the enzyme in the protein-polymer composite materials.

This relationship shows that bioactive proteins incorporated into solvent-borne protein-polymer composite materials had a similar initial specific activity within a broad range of solvents. However, in terms of stability, solvents having log P values in range of −0.5-2, inclusive, are used in processes described herein and allow for protein incorporation into solvent-borne coatings with optimum protein stability as shown by half-life times at 103° C. Solvents with log P 3.5 and higher, such as hexane and isooctane, are not compatible with the polyacrylate polyol resins used in embodiments of processes of making two component solvent-borne (2K SB) polymer-protein composites of the present invention.

While some embodiments include use of a non-aqueous organic solvent having a log P in the range of −0.5-2, inclusive, solvents having a lower or higher log P could also be used if they are compatible with resins and bioactive proteins.

Non-limiting examples of solvents having log P values ranging from −0.5 to 2, inclusive, include methyl ethyl ketone (0.29), ethyl acetate (0.7), methyl isobutyl ketone (1.31), butyl acetate (1.7) and other solvents listed in Table 2.

A non-aqueous organic solvent having a log P in the range of −0.5-2 inclusive, can be any such solvent compatible with polymer resins and not substantially reactive with a selected crosslinker to be used in a process of the present invention. Examples of non-aqueous organic solvents incompatible with polyacrylate polyol polymer resins and polyisocyanate crosslinkers are aliphatic hydrocarbons and non-aqueous organic solvents having hydroxyl and/or amino groups. Thus, in some embodiments, aliphatic hydrocarbon non-aqueous organic solvents and non-aqueous organic solvents having hydroxyl and/or amino groups are excluded as not compatible with polymer resins used in inventive processes.

TABLE 2

Solvents having log P values in the range of −0.5-2

| Solvent | Log P |
|---|---|
| acetone | −0.23 |
| butanone | 0.29 |
| ethyl acetate | 0.68 |
| pentanone | 0.8 |
| cyclohexanone | 0.96 |
| methyl propionate | 0.97 |
| propylacetate | 1.2 |
| ethyl chloride | 1.3 |
| hexanone | 1.3 |

TABLE 2-continued

Solvents having log P values in the range of −0.5-2

| Solvent | Log P |
|---|---|
| methyl cyclohexanone | 1.5 |
| benzyl acetate | 1.6 |
| butyl acetate | 1.7 |

It is a surprising finding of the present invention that protein-polymer composite materials retain bioactive protein activity when the curable composition is exposed to elevated temperatures, such as a temperature over 37° C., wherein the temperature is compatible with curing the polymer component included in the composite. In general, it has been believed that exposure of bioactive proteins to temperatures over 37° C. contributes to loss of bioactivity, for instance due to denaturation of the proteins. Without wishing to be bound by theory, it is believed that exposure of the curable composition to a temperature over 37° C. increases and/or accelerates covalent bonding of the bioactive proteins and the polymer or crosslinker. It is known that enzymes tend to denature at high temperature, if no method is provided to prohibit this process. However, it is found that the curing process at high temperature, such as 80° C. for 30 minutes as described in Examples herein, exerts insignificant influence on the incorporated enzymatic activity, indicating the faster formed polymeric matrix at high temperature contributes to the stabilization of the incorporated enzyme via multi-point linkages and confinement. The faster evaporation rate of unfavored solvents at high temperature might also contribute to enzyme activity retention.

Thus, in particular embodiments, the curable composition is exposed to a temperature over 37° C., for a period of time sufficient to decrease leaching of bioactive proteins from the cured composition. Leaching is measured by well-known methods such as those described in the Examples herein.

Figure 2:
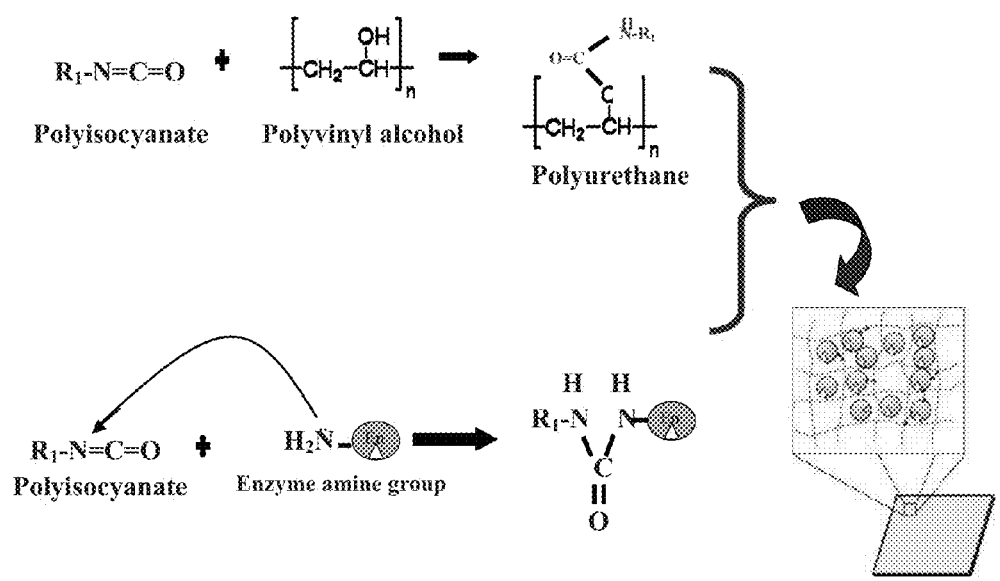
FIG. 2 is a schematic illustration of incorporation of bioactive proteins by covalent bonding of the bioactive proteins and the polymer or crosslinker as well as by physical entrapment of the proteins.

FIG. 2 is a schematic illustration of incorporation of bioactive proteins by covalent bonding of the bioactive proteins and the polymer or crosslinker as well as by physical entrapment of the proteins.

Protein-polymer composite materials are provided according to embodiments of the present invention which include bioactive proteins dispersed in a two component solvent-borne polymer resin. In embodiments of protein-polymer composite materials, the average particle size of bioactive protein particles in the protein-polymer composite material is less than 10 μm (average diameter) such as in the range of 1 nm to 10 μm, inclusive.

In particular embodiments, protein-polymer composite materials produced according to the present invention are protein-polyurethane composite materials.

A curable composition formed by a process described herein is applied to a substrate to form a bioactive coating of protein-polymer composite material according to embodiments of the present invention.

Typically, the coating is applied to produce a coating having a thickness in the range of about 1-500 microns when dry, although coatings thicker or thinner can be used depending on the desired use.

Application of the curable composition is accomplished by any of various methods illustratively including spray coating, dip coating, flow coating, roller coating and brush coating.

A substrate is any of various substrates to which a coating is advantageously applied. For example, a substrate is a sheet material. In a further example, a substrate is a vehicle part, such as a vehicle body panel, a cooking surface, clothing, thread material, or other desired material.

Substrates for use according to the present invention include, but are not limited to, metal substrates, silica, substrates, plastic substrates such as polyester substrates, cotton substrates, and glass substrates, or substrates incorporating combinations thereof.

A substrate optionally includes a coating such as a primer, a primer-surfacer, a primer-sealer, a basecoat, an adhesion promoting layer; or a combination of any of these or other surface treatment coatings.

Bioactive coatings of protein-polymer composite material according to embodiments of the present invention provide good adhesion to substrates, protection against environmental insults, protection against corrosion, and further provide bioactive properties of the bioactive protein. Thus, bioactive coatings of protein-polymer composite material according to embodiments of the present invention provide enzyme activity on a substrate useful in numerous applications such as detection of an analyte which is a substrate for the enzyme or a ligand for a receptor, antibody or lectin. In particular embodiments, bioactive coatings provide resistance against staining by enzyme digestion of one or more components of stain producing material.

Coatings optionally have a surface activity of at least 0.1 Unit/$cm^2$. Surface activity is defined as the enzyme units present in square centimeter of surface area. In some embodiments surface activity is within any range or at any point at or between 0.1 and 2.5 units/$cm^2$ inclusive.

Embodiments of the invention are illustrated in the following examples. These examples are provided for illustrative purposes and are not considered limitations on the scope of the invention.

EXAMPLE 1

Direct Dispersion of Protein Solution to Make Solvent Borne (SB) Polyurethane (PU) Coatings In a typical preparation, an amylase is first dissolved in DI water at a concentration up to 200 mg/ml. For some enzymes, such as α-amylase (KLEISTASE SD80 from Amano Enzyme Inc.) with large amount of impurities, filtration or centrifugation is required to remove the insoluble solids before use for coating preparation. Specifically the starch impurity in raw powder is removed by filtration over a 200 nm PTFE filter to obtain a purified α-amylase enzyme solution with a protein content of 200 mg/ml. Hydroxyl-functioned polyacrylate resin (2.1 g of Desmophen A 870 BA from Bayer Corp.) is diluted with a selected solvent at a weight ratio of 2:1 and then mixed with a silicone surfactant polyether modified polydimethylsiloxane (0.1 ml of BYK 333 solution in n-butanol, 17% wt) and enzyme solution (0.6 ml) in a 20-ml glass vial followed by vigorous stirring for 1 min at 2000 rpm, followed by the addition of 0.8 g of Desmodur N 3600 (Bayer Corp.), hexamethylene diisocyanate, and mixing for another 1 minute. Coating is formed by applying the mixed composition onto a pre-cleaned aluminum testing panel with a 8-path wet film applicator (Paul N. Gardner, Pompano Beach, Fla.) in the predetermined thickness of 2 mils (50.8 μm) onto aluminum testing panels (Paul N. Gardner, Pompano Beach, Fla.) (previously cleaned with acetone), and cured first at 80° C. for 30 minutes and then at ambient temperature for 1 week.

WB coatings containing α-amylase are prepared beginning with 2 ml of deionized water containing 45 mg α-amylase processed as described above to form an operating protein solution of 20 mg/m. Bayhydrol XP 7093 polyester emulsion resin 1.5 g is weighted and mixed with 1.5 ml of protein solution and 361 μl surfactant BYK 333 (17% w/v in 1-butanol) and mixed for 1 minute. Water dispersible diisocyanate curing agent Bayhydrol 302 0.6 g is then added and the resulting solution mixed for another 1 minute. The mixture was then immediately drawn down onto aluminum testing panels via 8-path wet film applicator (Paul N. Gardner, Pompano Beach, Fla.) in the predetermined thickness of 2 mil and cured in the oven at 80° C. for 30 min followed by 3 days storage.

Similar coatings are prepared using β-amylase, γ-amylase, six different analogues of α-amylase, or combinations of α-amylase and β-amylase at similar protein concentrations.

EXAMPLE 2

Activity Assays for Native and Incorporated Enzymes

The activity of α-amylase is measured using a colorimetric assay based on the detection of sugars (mainly maltose) released from the enzyme-catalyzed decomposition of starch substantially akin to the colorimetric assay of Fischer and Stein, *Biochem. Prep.* 8, 27-33 (1961). The substrate solution is first prepared by dissolving potato starch in 20 mM, pH 6.9 sodium phosphate buffer containing 6.7 mM sodium chloride. In a typical assay, a 10-μl aliquot of α-amylase solution is incubated with 1 ml of substrate solution for 3 minutes at room temperature. Subsequently 1 ml of the 3,5-dinitrosalicylic acid solution is then added. The reaction is stopped by incubating the reaction vial in the boiling water for 15 minutes, followed by cooling in an ice bath. The equivalent of reducing sugar is determined by the absorbance change at 540 nm. One unit of α-amylase activity is defined as 1.0 mg of reducing sugar (calculated from a standard curve previously calibrated against maltose) released from starch in 3 minutes at 25° C., pH 6.9.

The activity of α-amylase in a coating of a protein-polymer composite material is determined in a similar manner except one piece of sample panel coated with α-amylase or an analog of α-amylase (1.2×1.9 $cm^2$) prepared in Example 1 is used instead of the enzyme solution. Before every activity test, the coating is extensively rinsed with DI water at least 5 times to remove physically absorbed enzymes. The rinse solutions are collected, and the protein content in the rinse solution is determined by Bradford reagent to calculate the protein loading in the coating, which is ~150 μg protein/$cm^2$ in the case of α-amylase containing SB PU coating.

EXAMPLE 3

Effect of Solvent Type on the Surface Activity of Amylase-Containing SB PU Coatings α-Amylase-Containing SB PU Coatings are Prepared Following the Same Procedure as described in Example 1, except that a solvent with different log P values, including acetone (−0.23), methyl ethyl ketone (0.29), ethyl acetate (0.7), methyl isobutyl ketone (1.31) butyl acetate (1.7), toluene (2.7), hexane (3.5) or isooctane (4.5), is used to dilute the resin before the addition of enzyme solution. The performance of the resulting coatings, in terms of surface activity and stability, is evaluated and summarized in Table 1. While little impact is found on the initial surface activity, the solvent type affects enzyme stability. For example, in log P value ranging from −0.23 to 1.7, the half life time of the incorporated α-amylase at 103° C. increases consistently. However, with toluene (log P=2.5) as the diluting solvent, it drops sharply, yet enzyme activity remains.

EXAMPLE 4

Thermostability of Native and Incorporated α-Amylase at Different Temperatures—a Comparative Study The thermostability of α-amylase based bioactive coating prepared as in Example 1 is determined at specified temperatures ranging from ambient temperature (23° C.) to extremely high temperature of 120° C. After specific periods of aging in a gravity oven, the activity of samples of free enzyme and enzyme-containing coatings are evaluated as in Example 2.

Figure 3:
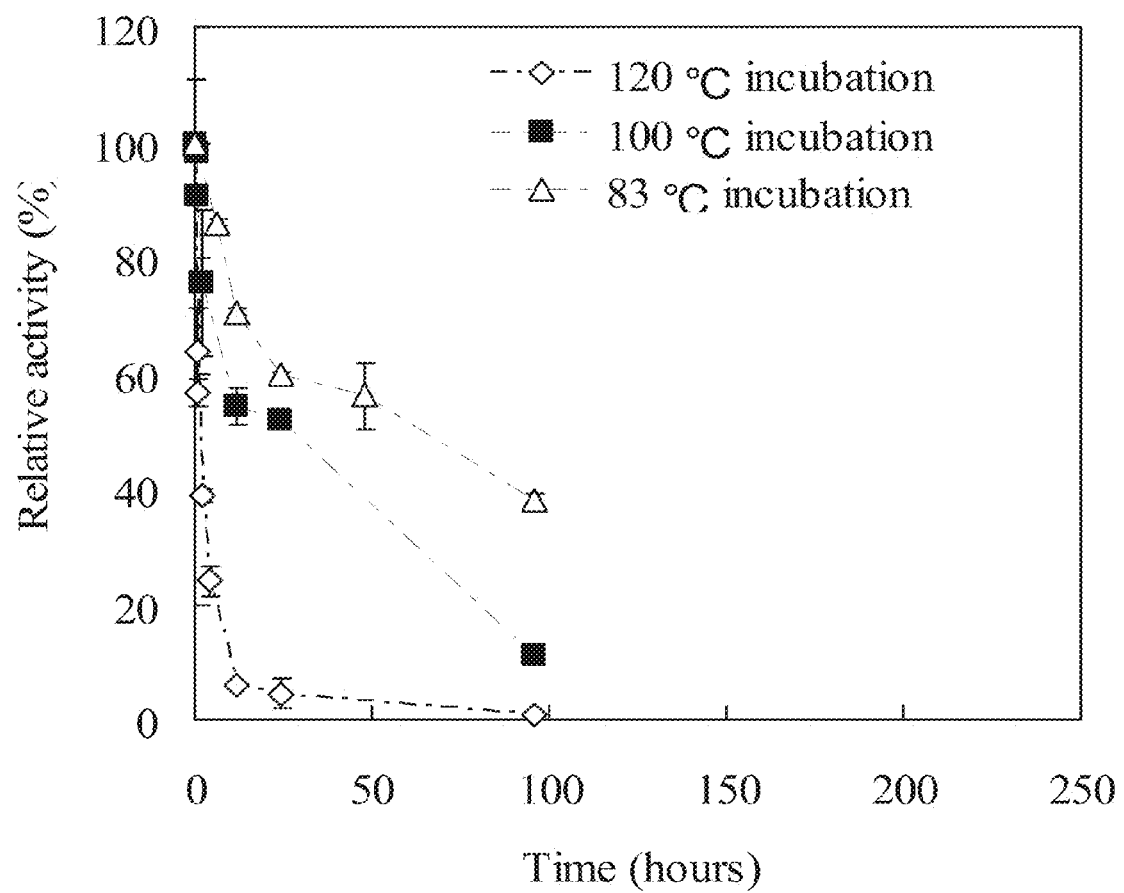
FIG. 3 is a graph showing thermostability of native α-amylase.
Figure 4:
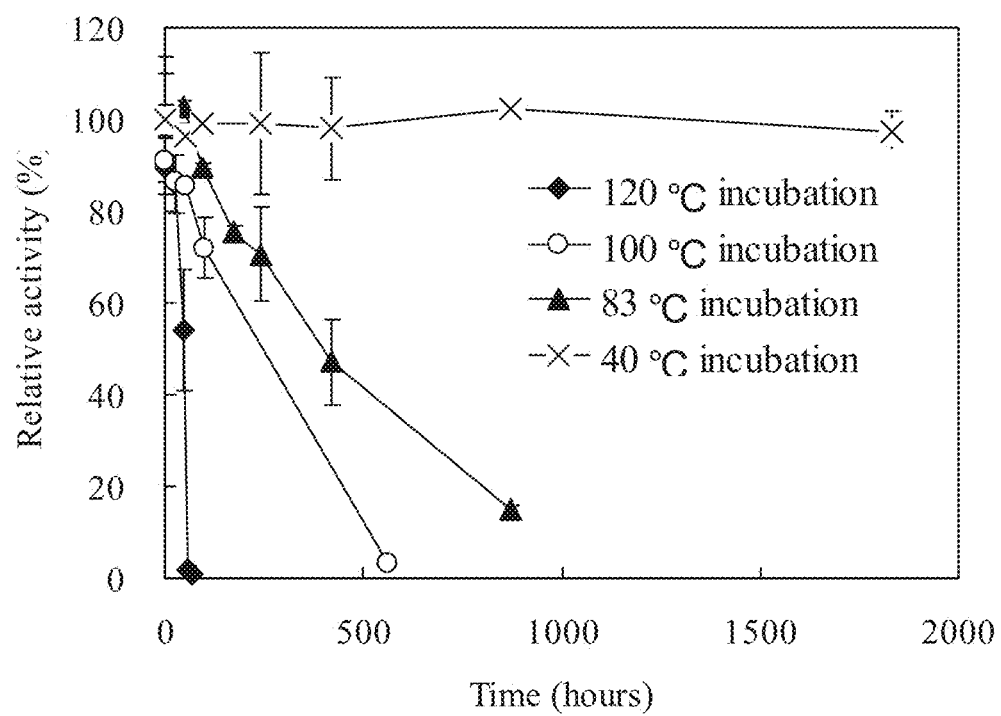
FIG. 4 is a graph showing thermostability of α-amylase incorporated in a two component solvent-borne polyurethane (2K SB PU) coating produced according to embodiments of the present invention.

The thermostability of native and incorporated α-amylase at different high temperatures ranging from 40, 83, 100 and 120° C. are illustrated in FIGS. 3 and 4, respectively. Compared to native enzyme, the heat-resistance of the enzyme incorporated in SB PU coatings has been greatly enhanced. Estimated half-life times of the incorporated α-amylase are about 460, 200, 31 hours at 83, 100 and 120° C., whereas the half-lives of the freely unbound native counterparts are about 50, 19, 1 hours, respectively. No significant loss of activity for incorporated enzyme is observed while incubating at relatively low temperatures such as 40° C. as shown in FIG. 4 with the estimated half-life as long as 660 days.

Figure 5:
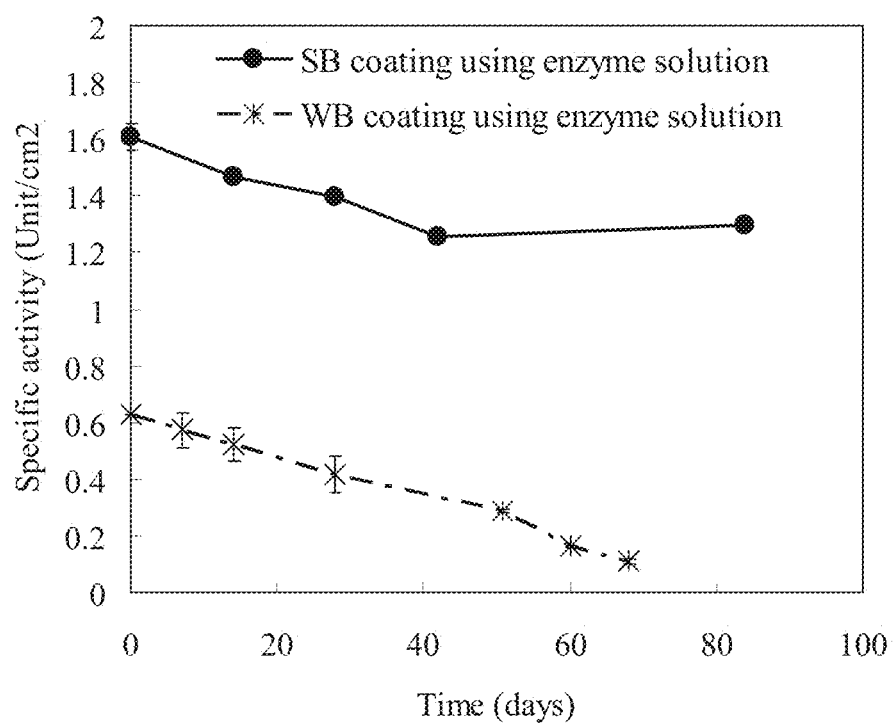
FIG. 5 is a graph illustrating long-term stability of incorporated α-amylase in different types of polyurethane (PU) coatings at ambient temperature.
Figure 6A:
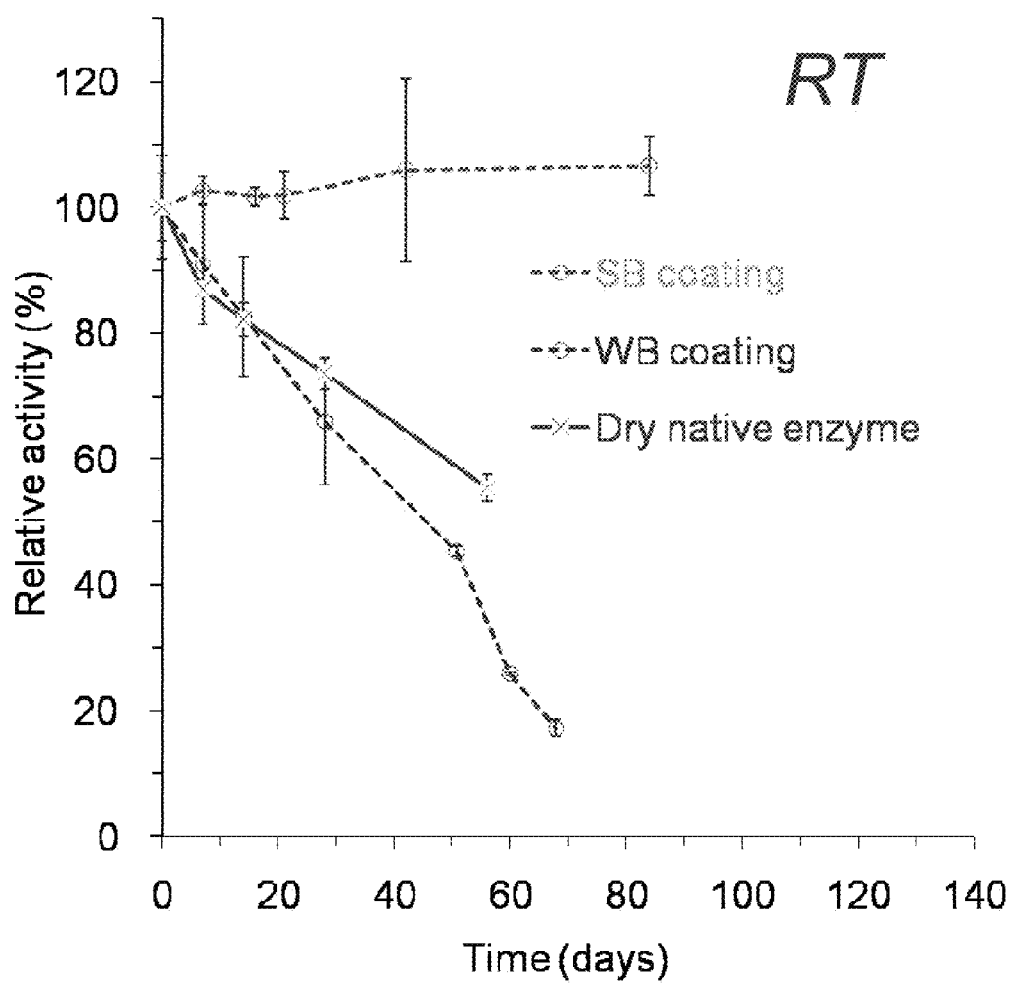
FIG. 6A is an illustration of relative activity of α-amylase alone, incorporated in a two component solvent-borne polyurethane (2K SB PU) coating, or incorporated in a two component water-borne coating at ambient temperature.
Figure 6B:
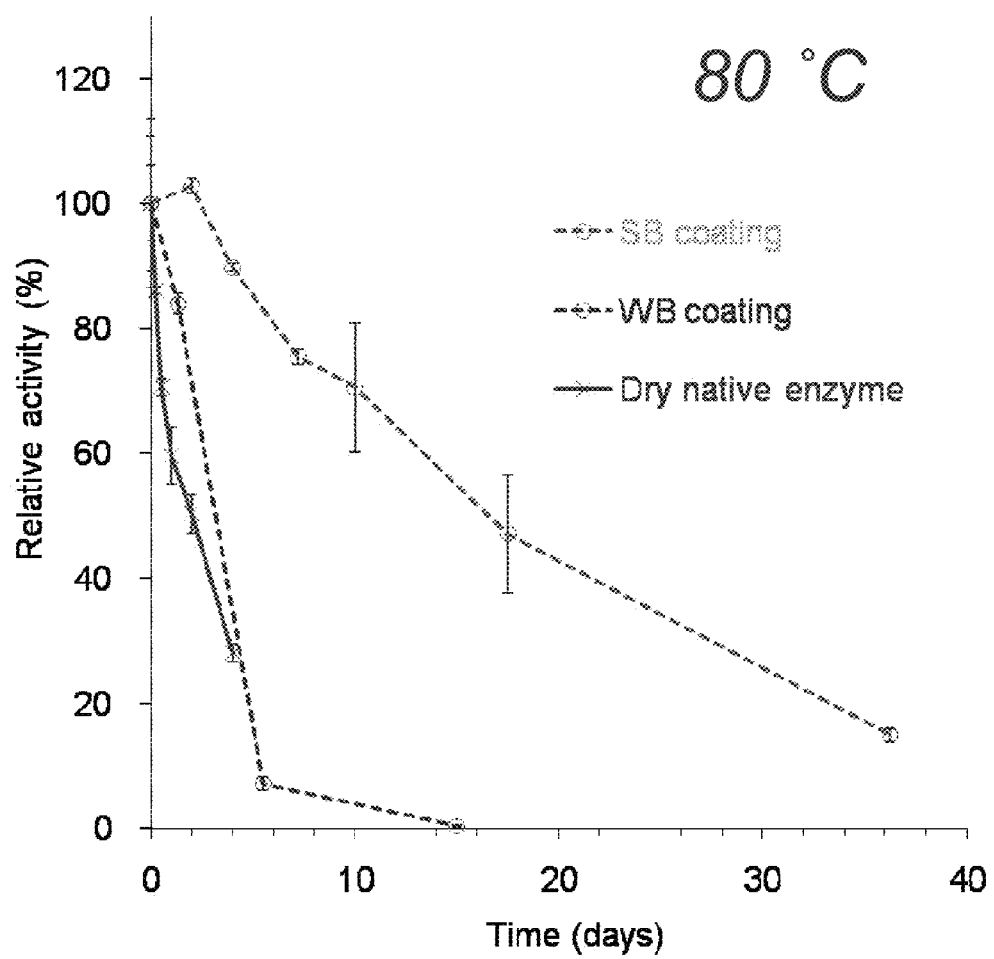
FIG. 6B is an illustration of relative activity of α-amylase alone, incorporated in a two component solvent-borne polyurethane (2K SB PU) coating, or incorporated in a two component water-borne coating at elevated temperature.

The enzyme in SB coatings affords better protection to enzyme molecules as compared to water borne (WB) coatings. 2K WB PU coatings containing α-amylase are prepared as follows: 1.5 g of Bayhydrol XP 7093 (from Bayer Corp.) polyester resin is first mixed with equal volume of enzyme solution (20 mg/ml) and 0.36 ml of surfactant BYK 333 (17% w/v in 1-butanol) to form Part A, which was added into Part B, the curing agent-water dispersible diisocyanate (Bayhydrol 302 from Bayer Corp., 0.6 g). After mixing for 1 minute, the coating is prepared and cured following the same procedure for SB coatings as described in Example 1. As shown in FIG. 5, enzymes incorporated into SB PU coatings retain their relative activity over 85% after 3 months, whereas the enzymes in water-borne (WB) PU coatings show a constant decrease of activity with a half life of about 50 days. The increased stability of α-amylase in SB PU coatings is observed at both ambient temperature and elevated temperature of 80° C. as shown in FIGS. 6A and B.

EXAMPLE 5

Enzyme Distribution in SB-PU Coating

The distribution of α-amylase in the SB PU coatings prepared as described in Example 1 is characterized using fluorescent dye labeling, SEM, and confocal laser scanning microscopy (CLSM). The enzyme-containing coating is dyed in 5 µM of Oregon Green 488 Maleimide for 16 hrs at 4° C. in dark and then rinsed with pH 7 phosphate buffer for 2 hrs at room temperature. A Prolong Gold anti-fade reagent is used when loading the sample onto the microscope. As controls, coatings without enzyme are prepared and examined following the same procedure. Images are taken with an objective lens of 63× with water immersion. The excitation and max emission wavelengths are 488 nm and 524 nm, respectively.

For SEM analyses, the surface as well as the cross-section of bioactive coatings is observed using a Hitachi S-3500 N SEM (Mahwah, N.J.). Samples are prepared by layering the coatings of Example 1 on aluminum foil following the same protocol as given for the aluminum panels. The fully cured coatings are torn and the resulting cross-section of the fractured polymer and surface are sputtered with Au—Pd.

Figure 7:
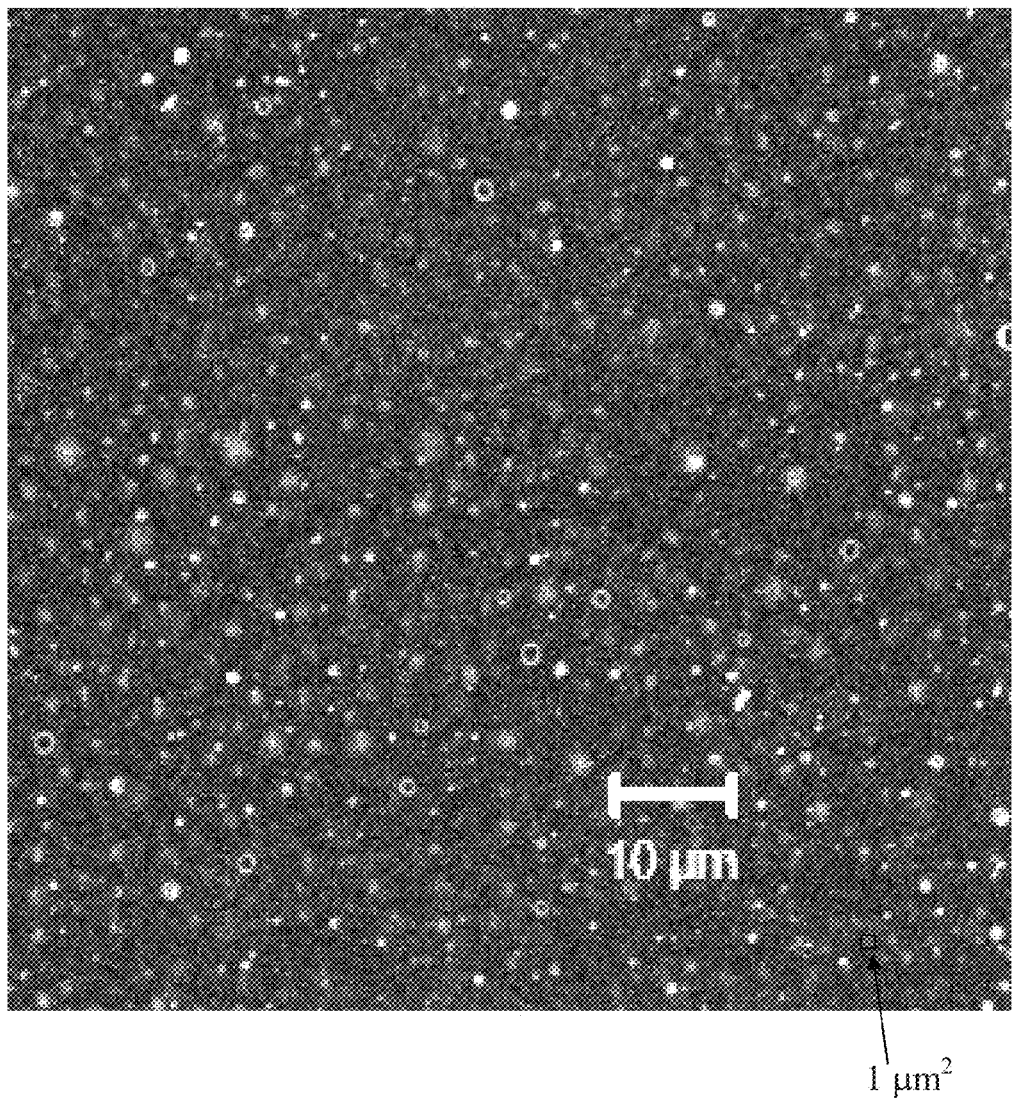
FIG. 7 is a confocal laser scanning microscopic image of 2K SB PU containing α-amylase at a depth of ~2 μm from the top surface.
Figure 8:
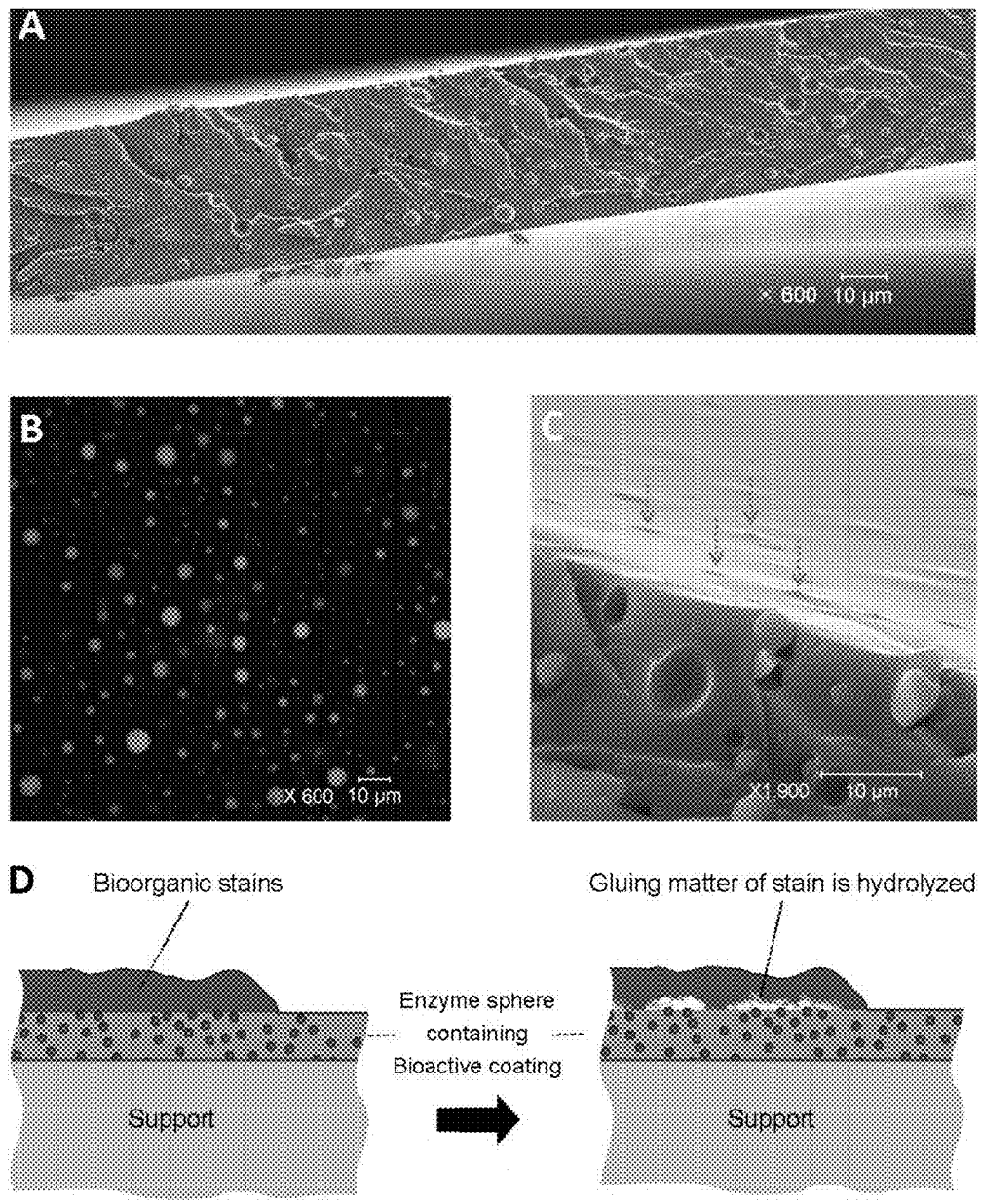
FIG. 8 illustrates SEM-EDS analysis (A) and CLSM after labeling the enzyme with Oregon Green™ (B) of α-amylase in a fully cured two component solvent-borne polyurethane (2K SB PU) coating where protein pockets are localized to the coating surface (C); the presence of protein on the surface facilitates breakdown of surface stains as illustrated by schematic (D)

As shown in FIGS. 7 and 8, the enzyme molecules are dispersed in the coatings in the form of small particles with size ranging from submicron to a few micrometers.

EXAMPLE 6

Amylase Containing Coatings Facilitate Removal of Bioorganic Stains

Common BBQ, tartar sauce, and light mayonnaise (i.e. Kraft Honey BBQ, Kraft Tartar sauce, and Kraft light mayonnaise) as well as egg white and chicken blood are obtained from a grocery store. Three types of coated panels are analyzed: 1) enzyme-free PU coating, 2) BSA-containing PU coating (prepared as described with the exception that BSA is used at a concentration of 100 mg/mL in place of the amylase) as negative control and 3) α-amylase containing coatings prepared as in Example 1 to a surface enzyme activities of 0.05 to 0.22 mg/cm$^2$. Each alumina panel (0.6×76×152 mm$^3$), or wooden table surface, is overlaid with a template of ten uniform punched-out holes (diameter=0.9 cm) wherein 100 µL of each bioorganic material is directly applied as stain spot. The excess stain is scraped off using a spatula. Stains are dried on a plate heated up to 40° C. for 45 min. After drying, panels with dry stain spots are face-up immersed into a deionized water bath with 200 rpm horizontal shaking. The time course of removing the stain spots is monitored for quantitative analysis.

Figure 9:
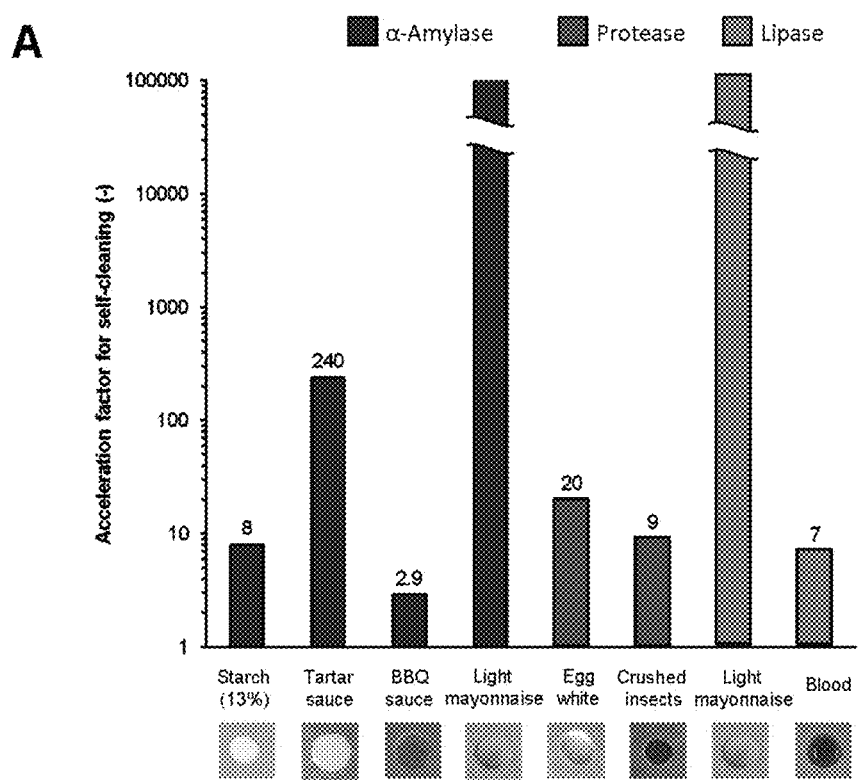
FIG. 9 is a depiction of facilitated bioorganic stain removal by coatings containing various proteins.
Figure 10:
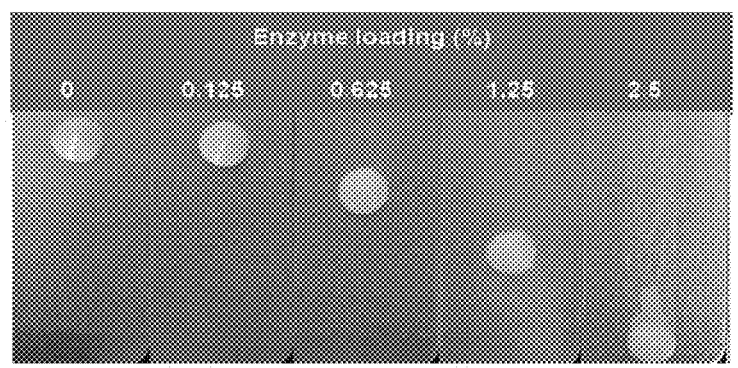
FIG. 10 illustrates facilitated stain removal by coatings with varying concentrations of α-amylase under various experimental conditions (A) and (B)
Figure 10:
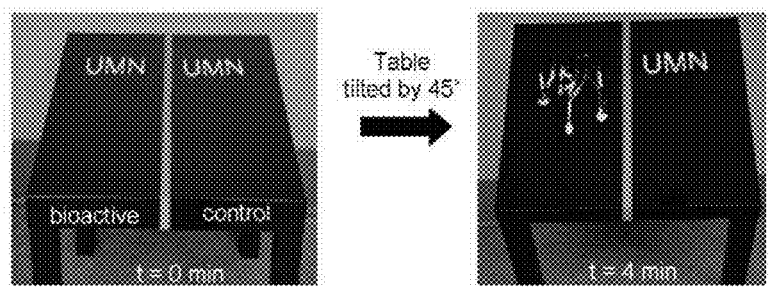

Amylase, lipase, or protease containing coatings accelerate the rinsing time by as much as $10^4$ in comparison to control coatings (FIG. 9). Light mayonnaise stains that contain high-amylose starch for texturizing are detach from the amylase containing coated surface within one minute when the coated surface is tilted by 45° (FIG. 10) whereas the light mayonnaise on BSA containing coatings remain adhered to the coating surface (FIG. 10B).

HPLC analyses demonstrate that α-amylase is enzymatically breaking down starch components such as that contained in light mayonnaise. Wheat starch solution is prepared to a final concentration of 10% w/v deionized water. The starch solution (100 µl) is applied onto an α-amylase containing coating on an aluminum panel prepared as in Example 1 and incubated for 0 min, 10 min, 60 min, or 90 min followed by removal with 9.9 mL deionized water and collection of the rinsate. Rinsate is diluted 100 times followed by centrifugation and filtration over NanoSEP filter (Pall, East Hills, N.Y.) with a cut-off 30 KDa at 16000 rpm for 1 min, and analyzed by HPLC chromatograph (Varian, Walnut Creek, Calif.). Separation of starch components is performed with a Varian Metacarb 87P (300×7.8 mm) column (Varian, Walnut Creek, Calif.) using HPLC grade water as eluent (flow rate 0.4 ml/min; 80° C.; running time 45 min). Various analytes are detected via a ELSD (Polymer Laboratories 2100 ELSD, Amherst, Mass.) calibrated with purified carbohydrates.

Figure 11:
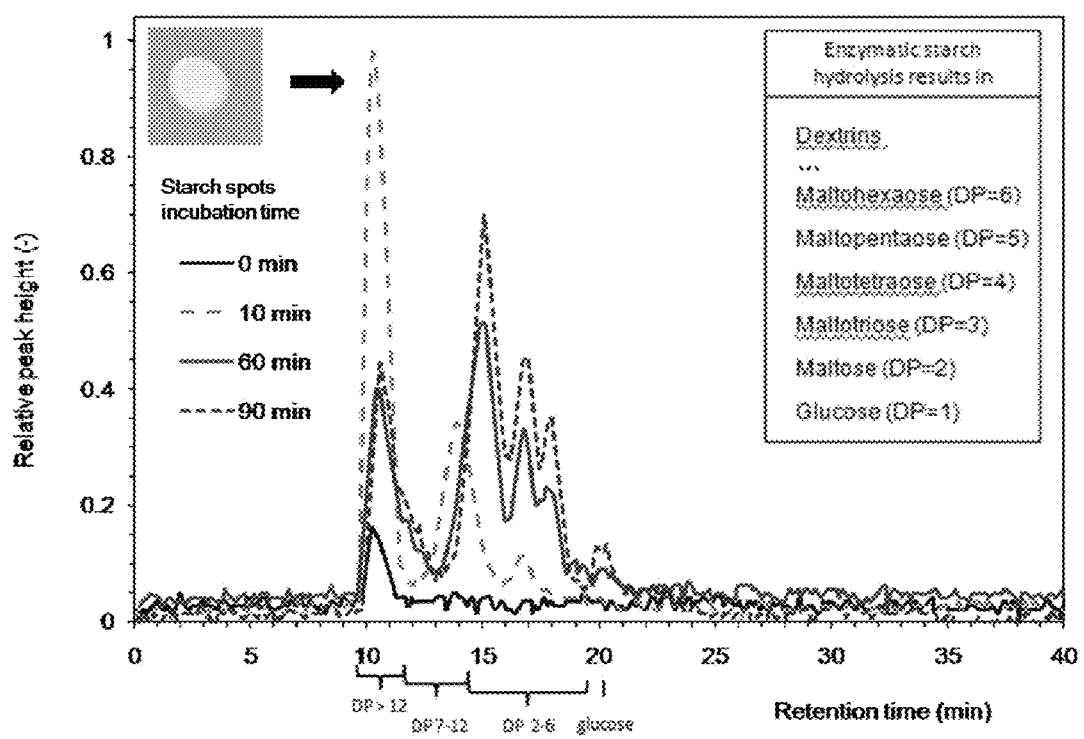
FIG. 11 illustrates HPLC analyses of breakdown products by starch containing bioorganic stains by α-amylase containing coatings.

Fractions of increasing levels of small molecules consisting of peaks with retention times of 15-20 minutes are observed in samples with increased incubation time on the coatings. The sizes of observed breakdown products are reduced as a function of stain-coating contact time (FIG. 11).

It is appreciated that all reagents are obtainable by sources known in the art unless otherwise specified or synthesized by one of ordinary skill in the art without undue experimentation. Methods of nucleotide amplification, cell transfection, and protein expression and purification are similarly within the level of skill in the art.

Methods of cloning, expressing, and purifying any protein operable herein is achievable by methods ordinarily practiced in the art illustratively by methods disclosed in Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002, the contents of each of which are incorporated herein by reference.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The compositions and processes described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A protein-polymer composite material, comprising:
one or more amylases dispersed in a two component non-aqueous organic solvent-borne polymer resin, said amylase in the form of a particle with an average particle size, wherein said average particle size in the protein-polymer composite material is in the range of 10 μm (average diameter) or less.

2. The material of claim 1, wherein said resin comprises a hydroxyl-functionalized acrylate resin.

3. The material of claim 1 wherein said resin comprises a polyisocyanate crosslinker.

4. The material of claim 1 wherein said amylase is an α-amylase.

5. The material of claim 1 further comprising one or more additives.

* * * * *